(12) United States Patent
Emonds et al.

(10) Patent No.: US 6,362,335 B2
(45) Date of Patent: Mar. 26, 2002

(54) PROCESS FOR THE PREPARATION OF 2-AMINO-5,8-DIMETHOXY(1,2,4)TRIAZOLO (1,5C)PYRIMIDINE

(75) Inventors: Mark Victor Michael Emonds; Gary A. Roth, both of Midland, MI (US)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

(21) Appl. No.: 09/882,657

(22) Filed: Jun. 15, 2001

Related U.S. Application Data

(60) Provisional application No. 60/212,024, filed on Jun. 16, 2000.

(51) Int. Cl.[7] .............................................. C07D 487/04
(52) U.S. Cl. ...................................................... 544/263
(58) Field of Search ......................................... 544/263

(56) References Cited

U.S. PATENT DOCUMENTS 5,858,924 A    1/1999    Johnson et al. ............. 504/241

*Primary Examiner*—John M. Ford
(74) *Attorney, Agent, or Firm*—Craig E. Mixan

(57) ABSTRACT

2-Amino-5, 8-dimethoxy[1,2,4]triazolo[1,5-c]-pyrimidine is prepared from a 5-chloro or 5-methoxy substituted 3-amino-8-methoxy[1,2,4]triazolo[4,3-c]-pyrimidine by reaction with methoxide in an alcohol solvent. Both rearrangement and, when the 5-substituent is chloro, methoxy substitution can be accomplished directly.

4 Claims, No Drawings

PROCESS FOR THE PREPARATION OF 2-AMINO-5,8-DIMETHOXY(1,2,4)TRIAZOLO (1,5C)PYRIMIDINE

This Appln claims benefits of Prov. No. 60/212,024 filed Jun. 16, 2000.

BACKGROUND OF THE INVENTION

The present invention concerns a process for the preparation of 2-amino-5,8-dimethoxy[1,2,4]-triazolo[1,5-c]pyrimidine.

U.S. Pat. No. 5,858,924 describes certain substituted benzenesulfonamide compounds and their use as herbicides. 2-Amino-5,8-dimethoxy[1,2,4]triazolo-[1,5-c]pyrimidine is a useful intermediate for the preparation of certain of these herbicides.

In U.S. Pat. No. 5,858,924, 2-amino-5,8-dimethoxy[1,2,4]triazolo[1,5-c]pyrimidine is prepared from 3-amino-8-methoxy-5-methylthio[1,2,4]triazolo-[4,3-c]pyrimidine by treatment with ethyl acrylate and sodium methoxide in methanol. The 3-amino-8-methoxy-5-methylthio[1,2,4]triazolo[4,3-c]pyrimidine in turn is prepared from 5-methoxy-4-chloro-2-methylthio-pyrimidine by treatment with hydrazine followed by cyclization with cyanogen bromide. It would be advantageous to produce 2-amino-5,8-dimethoxy[1,2,4]-triazolo[1,5-c]pyrimidine more efficiently and in higher yield. It would also be advantageous to avoid the use of methylthio containing intermediates and the use of ethyl acrylate in the rearrangement of a [1,2,4]triazolo[4,3-c]pyrimidine into a [1,2,4]-triazolo[1,5-c]pyrimidine.

SUMMARY OF THE INVENTION

The present invention concerns the preparation of 2-amino-5,8-dimethoxy[1,2,4]triazolo-[1,5-c]pyrimidine from a 5-chloro or 5-methoxy substituted 3-amino-8-methoxy[1,2,4]triazolo[4,3-c]-pyrimidine. More particularly, the present invention concerns a process for the preparation of a compound of the formula

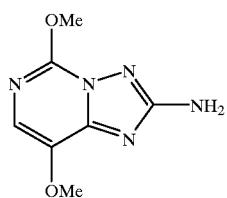

which comprises contacting a 3-amino-8-methoxy-[1,2,4]triazolo[4,3-c]pyrimidine of the formula

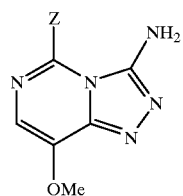

wherein Z represents Cl or OCH$_3$ with sodium or potassium methoxide in an alcohol solvent.

Another aspect of the present invention concerns a process for the preparation of

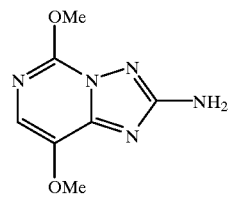

which comprises the steps of:

a) contacting a 5-methoxy-4-chloropyrimidine of the formula

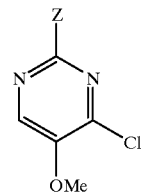

wherein Z represents Cl or OCH$_3$ with hydrazine and a base to prepare a 5-methoxy-4-hydrazinopyrimidine of the formula

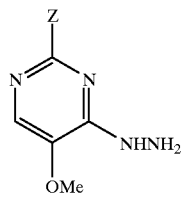

wherein Z is as previously defined;

b) contacting the 5-methoxy-4-hydrazinopyrimidine with cyanogen chloride or cyanogen bromide to prepare a 3-amino-8-methoxy[(1,2,4]triazolo[4,3-c]pyrimidine of the formula

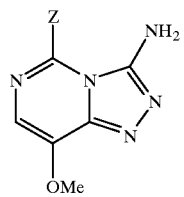

wherein Z is as previously defined; and c) contacting the 3-amino-8-methoxy[1,2,4]triazolo-[4,3-c]pyrimidine with sodium or potassium methoxide in an alcohol solvent.

DETAILED DESCRIPTION OF THE INVENTION

The rearrangement of the 3-amino-8-methoxy-[1,2,4]triazolo[4,3-c]pyrimidine of the formula

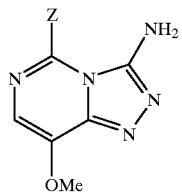

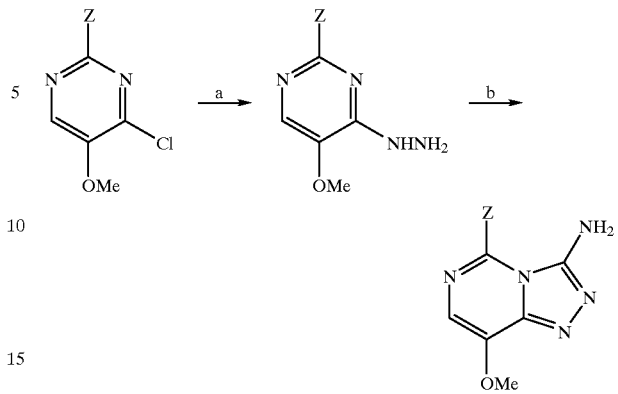

wherein Z represents Cl or OCH₃ to 2-amino-5,8-dimethoxy [1,2,4]triazolo[1,5-c]-pyrimidine is accomplished by treatment with sodium methoxide or potassium methoxide in an alcohol solvent.

For Z represents OCH₃, only a catalytically effective amount of methoxide is required, e.g., from about 0.01 to about 0.5 equivalents of methoxide per mole of [1,2,4]triazolo[4,3-c]pyrimidine. However, since the rate is dependent on the concentration of methoxide, the use of about 0.1 to about 0.5 equivalents of methoxide is usually preferred.

For Z represents Cl, an additional equivalent of methoxide is required to concomitantly convert the chloro substituent to a methoxide substituent. Thus, in this case, from about 1.1 to about 1.5 equivalents of methoxide is preferred.

The rearrangement is generally conducted in methanol as the solvent. Other primary and secondary alcohols may be used, however, depending on the reaction conditions, a significant amount of alkoxide exchange may occur at the 5-position of the triazolo-pyrimidine. Sterically hindered alcohols, for example tertiary-alcohols like t-butanol and t-amyl alcohol, may be used as the solvent resulting in little or no alkoxide exchange. Nevertheless, methanol is usually the preferred solvent. It is also possible to perform the rearrangement in the presence of additional diluents provided those diluents do not interfere with the desired reaction and are chemically inert to the reactants, particularly the methoxide base. A particularly suitable additional diluent is acetonitrile, which is often used as the solvent in the preparation of the [1,2,4]triazolo[4,3-c]-pyrimidine.

The rearrangement is conducted at a temperature from about 0° C. to the reflux temperature of the alcohol solvent. Temperatures from about 10° C. to about 35° C. are usually preferred.

The product is isolated by conventional techniques such as by filtration of a precipitated or crystallized material.

In a typical reaction, the 5-chloro or 5-methoxy substituted 3-amino-8-methoxy[1,2,4]triazolo-[4,3-c]pyrimidine is dissolved or suspended in alcohol and treated with the appropriate amount of sodium methoxide in methanol at ambient temperature. After the reaction is complete, the reaction mixture is diluted with water and the precipitated product is collected by filtration and dried. Optionally, some or most of the alcohol may be removed by distillation prior to filtration to improve crystal filtration or reduce solubility of the product in the solvent and therefore improve recovery.

The 5-chloro and 5-methoxy substituted 3-amino-8-methoxy[1,2,4]triazolo[4,3-c]pyrimidines can be conveniently prepared from the corresponding 2,4-dichloro-5-methoxypyrimidine(Chesterfield, J., McOmie, J. F. W., Sayer, E. R., "Pyrimidines. Part VIII. Halogeno- and Hydrazino-pyrimidines" *J. Chem. Soc.* 1955, 3478–3481) and the 2,5-dimethoxy-4-chloro-pyrimidine respectively by a) the reaction with hydrazine and base followed by b) reaction with cyanogen chloride or cyanogen bromide.

During the reaction with hydrazine in step a), a base is required to neutralize the hydrogen chloride produced. This base may be an additional equivalent of hydrazine itself. However, it is often preferred to use an auxiliary base such as sodium or potassium carbonate, sodium or potassium hydroxide or a trialkylamine. Sodium carbonate is the preferred auxiliary base.

During the reaction with the cyanogen halide in the cyclization step b), hydrogen halide is produced. By using enough additional methoxide as base to neutralize the hydrogen halide given off, it is possible to accomplish both the methoxy substitution and/or the rearrangement as part of the work-up of the cyclization reaction. This process modification advantageously avoids the isolation of the [1,2,4]triazolo[4,3-c]pyrimidine.

The following examples are presented to illustrate the invention.

EXAMPLES

1. Preparation of 2,5-Dimethoxy-4-hydrazinopyrimidine

A slurry of 4-chloro-2,5-dimethoxypyrimidine (3.0 grams (g), 17.2 mmol) in methanol (15 milliliters (mL)) was treated with aqueous hydrazine (3.9 g of 35 wt. %, 42.5 mmol) in one portion causing a slow exotherm to 29° C. The reaction was then warmed to 50° C. and held at that temperature for 2 hours (h) at which time gas chromatography (GC) analysis indicated the reaction was complete. The clear solution was cooled to ambient temperature and allowed to stir overnight. The solvent was removed in vacuo and the resulting gummy solid was triturated with CH₃CN (50 mL). The resulting mixture was filtered through a pad of silica gel (6 centimeter (cm)×6 cm). The pad was rinsed with CH₃CN (550 mL). The filtrates were combined and the solvent removed in vacuo affording the title compound as a white solid (2.6 g, 89%): mp 115–117° C.; $^1$H NMR (300 MHz, DMSO-d₆) 3.73 (s, 3H), 3.76 (s, 3H), 4.29 (bs, 2H), 7.51 (s, 1H), 8.23 (bs, 1H); MS(GC, 70eV) 170 (M+, 100%), 155(55%), 151 (40%).

2. Preparation of 2-Chloro-4-hydrazino-5-methoxypyrimidine

Anhydrous sodium carbonate (5.83 g, 0.055 mole), methanol (60 mL), and 35% aqueous hydrazine (11.0 g, 0.120 mole) were loaded into a 500 mL three necked flask equipped with a thermometer, magnetic stirrer, condenser, and addition funnel. A solution/partial slurry of 2,4-dichloro-5-methoxy-pyrimidine (17.91 g, 0.100 mole) in toluene (30 mL) was added dropwise over 39 min. During the addition, the reaction temperature rose from 15° C. to 39° C. and the solids dissolved to form a clear, pale yellow solution. The reaction mixture was heated to 42° C. for 4.1 h, after which the heat source was removed. Slow, dropwise addition of water (180 mL), caused the product to crystallize out of solution. The resulting slurry was stirred for 2 h at room temperature, then the product was recovered by filtration through Whatman #1 filter paper using a Buchner funnel and aspirator vacuum. After washing the filter cake with water, the product was dried overnight in vacuo at 40° C., to give 15.02 g of white 2-chloro-4-hydrazino-5-methoxypyrimidine (purity 96.2%, yield=82.8%): $^1$H NMR (300 MHz, DMSO-$d_6$) 3.33 (s, 3H), 3.78 (s, 3H), 4.39 (br s, 2H), 7.59 (s, 1H), 8.73 (br s, 1H).

3. Preparation of 2-Chloro-4-hydrazino-5methoxy-pyrimidine

Anhydrous sodium carbonate (29.15 g, 0.275 mole), methanol (300 mL), and 35% aqueous hydrazine (54.9 g, 0.60 mole) were loaded into a 1 L glass jacketed reactor equipped with a thermocouple temperature probe, overhead stirrer with glass agitator, condenser, and a programmable circulating bath. 2,4-Dichloro-5-methoxypyrimidine (89.50 g, 0.50 mole) was added as a solid in small increments over 70 min. During the addition, the reactor jacket was kept at 20° C., and the reaction temperature rose from 21° C. to 28° C. Upon completion of the addition, the reaction mixture was heated to 43° C. over 60 min, then held at 43° C. for 4.5 h. Water (300 mL) was then added, and a distillation head was attached to the reactor. Vacuum was applied to lower the pressure to 140 mmHg, and methanol was removed by distillation. Distillation continued for 1.5 h, at which point the rate of distillation had slowed greatly. The pressure as further decreased to 85 mmHg until water started to distill over, then vacuum was broken under a nitrogen flow. The reaction mixture was cooled from 43° C. to 25° C. over 60 min. The resulting slurry was stirred overnight at 25° C. The product was recovered by filtration through Whatman #52 filter paper using a Buchner funnel and aspirator vacuum. After washing the filter cake with water (221 g), the product was dried overnight in vacuo at 42° C., to give 83.5 g of white 2-chloro-4-hydrazino-5-methoxypyrimidine (purity 96.8%, yield=92.7%).

4. Preparation of 3-Amino-5-chloro-8-methoxy[1,2,4]-triazolo[4,3-c]pyrimidine

A 5 liter (L) 3-neck round bottom flask with thermowell was fitted with a condenser/N2 inlet, mechanical stirrer and an addition funnel. The pot was charged with 2-chloro-4-hydrazino-5-methoxypyrimidine (136 g of 70.7 wt. %, 96 g active, 0.55 mol) and isopropyl alcohol (IPA; 1100 mL). Cyanogen bromide (185 g of 34.6 wt. % in CH$_3$CN, 64 g active, 0.6 mol) was added rapidly causing a slow endotherm from 22 to 15° C. and then a slow exotherm to 27° C. During the exotherm the mixture goes through a very thick stage which lasts several minutes. The slurry was then warmed to 42° C. and held there for 3.5 h at which time high pressure liquid chromatography (HPLC) analysis indicated the reaction was complete. The slurry was cooled to room temperature and treated with a solution of Na$_2$CO$_3$ (64 g, 0.6 mol) in water (1100 mL) over a 30 minute (min) period causing the temperature to exotherm 4° C. The mixture was stirred at ambient temperature for 2 h and then the solid was collected by filtration. The filter cake was washed with water (400 mL) and then pressed as dry as possible under aspirator pressure. This provided the title compound (190.1 g of wet cake, 51 wt % by HPLC, 97 g active, 88%) as a brown solid. Drying a sample to a constant weight resulted in the following data: MS(GC, 70eV) 201(15%), 200 (30%), 199 (70%), 198 (100%); $^1$ H NMR (300 MHz, DMSO-$d_6$) 3.92 (s, 3H), 6.51 (br s, 2H), 7.11 (s, 1H).

5. Preparation of 3-Amino-5-chloro-8-methoxy[,2,4]-triazolo [4,3-c]pyrimidine

2-Chloro-4-hydrazino-5-methoxypyrimidine (10.75 g, 0.062 mole) was loaded into a 500 mL three necked flask equipped with a condenser, thermometer, and an overhead stirrer. IPA (125 mL) was added and the mixture was cooled to 13° C. using an ice bath. Cyanogen chloride (4.15 g, 0.068 mole) was added via cannula as a condensed liquid. The reaction mixture was heated to 41° C. for 3.5 h, then allowed to cool to room temperature. A solution of sodium carbonate (7.18 g) in water (125 mL) was added and the mixture was stirred for 2 h at room temperature in order to destroy any residual cyanogen chloride and neutralize the hydrochloride salts. The product was recovered by filtration through Whatman # 54 filter paper using a Buchner funnel and aspirator vacuum. It was washed with water, then dried overnight in vacuo to give 9.65 g of the title compound (yield=78.5%).

6. Preparation of 3-Amino-5,8-dimethoxy[1,2,4]-triazolo[4, 3-c]pyrimidine

4-Hydrazino-2, 5-dimethoxypyrimidine (8.522 g, 0.050 mole) was loaded into a 500 mL three necked flask equipped with an overhead stirrer, condenser, and thermocouple temperature probe. IPA (100 mL) was added and the mixture was stirred to form a slurry. A solution of cyanogen bromide (8.546 g, 0.081 mole) in acetonitrile (15 mL) was added, resulting in a 3° C. endotherm, followed by a 6° C. exotherm. The mixture wash heated to 42° C. for 3.5 h, then cooled to room temperature. A solution of sodium carbonate (5.92 g) in water (100 mL) was added, and the resulting mixture was stirred for 3.3 h. The product precipitated from the solution an d was recovered by filtration through Whatman #54 paper using a Buchner funnel and aspirator vacuum. The solids w ere dried overnight in vacuo at room temperature to give 8.516 g of 3-amino-5,8-dimethoxy[1,2, 4]triazolo[4,3-c]pyrimidine (yield=87.1%): mp=232–235° C. $^1$H NMR (300 MHz, DMSO-$d_6$) 3.83 (s, 3H), 3.97 (s, 3H), 6.45 (br s, 2H), 6.84 (s, 1H); $^{13}$C NMR (75.47 MHz, DMSO-$d_6$) 55.4, 56.4, 115.5, 139.7, 142.0, 142.5, 148.3.

7. Preparation of 2-Amino-5,8-dimethoxy[1,2,4]-triazolo [1,5-c]pyrimidine

3-Amino-5,8-dimethoxy[1,2,4]triazolo[4,3-c]-pyrimidine (9.762 g, 0.050 mole) was loaded into a 500 mL three necked flask equipped with an overhead stirrer, condenser, addition funnel, and thermocouple temperature probe. Methanol (70 mL) was added and the mixture was stirred to form a slurry. Sodium methoxide (16.716 g of a 25% solution in methanol) was added dropwise over 28 min, after which the mixture was stirred at room temperature for 3 h. The reaction mixture was then diluted with water (135 mL) and stirred for an additional 1.5 h. The product solids were recovered by filtration through Whatman #54 paper using a Buchner funnel and aspirator vacuum. After washing with water, the solids were dried in vacuo at room temperature to give 9.064 g of 2-amino-5,8-dimethoxy[1,2,4]triazolo[1,5-c]pyrimidine (yield=92.8%): $^1$H NMR (300 MHz, DMSO-$d_6$) 3.88 (s, 3H), 4.04 (s, 3H), 6.38 (br s, 2H), 7.48 (s, 1H); MS(GC, 70eV) 195 (M+, 85%), 194 (100%)

8. Preparation of 2-Amino-5,8-dimethoxy[1,2,4]triazolo[1, 5-c]pyrimidine

2-Chloro-4-hydrazino-5-methoxypyrimidine (15.62 g of 83.8% pure chlorohydrazinomethoxy-pyrimidine=13.09 g actual chlorohydrazinomethoxy-pyrimidine, 0.075 mole) was loaded into a 500 mL three-necked flask equipped with a magnetic stirrer, a condenser, a thermometer, and an addition funnel. tert-Butyl alcohol (150 mL) was added and the mixture was stirred to give a white slurry. A solution of cyanogen bromide (8.78 g, 0.083 mole) in acetonitrile (20 mL) was added dropwise over 13 min. The temperature of the mixture decreased from 23° C. to 22° C. The reaction mixture was then heated to 43° C. or 5.2 h. The reaction mixture (a light yellow slurry) was then carefully transferred by a Teflon™ cannula into a second 500 mL three necked flask containing 25% sodium methoxide in methanol (41.5 g, 0.188 mole). Transfer took place over 52 min, and resulted in the reaction temperature increasing from 21° C. to a maximum of 42° C. The resulting reaction mixture was a dark olive green slurry. A sample taken 2 min after the completion of the addition and analyzed by HPLC showed the conversion of intermediate 3-amino-5-chloro-8-methoxy [1,2,4]triazolo[4,3-c]-pyrimidine to the desired final product 2-amino-5,8-dimethoxy[1,2,4]triazolo[1,5-c]pyrimidine to be 99% complete. After 30 min, the reaction mixture was diluted with water (300 mL) added over 12 min. The resulting slurry was stirred for 1 h, then the solids were collected by filtration through Whatman #1 paper using a Buchner funnel and aspirator vacuum. The solids were washed with water, then dried overnight in vacuo at 48° C. to give the product as a grayish green-blue solid (11.99 g of 91.3% pure 2-amino-5,8-dimethoxy[1,2,4]triazolo[1,5-c] pyrimidine, 74.7% yield).

9. Preparation of 2-Amino-5,8-dimethoxy[1,2,4]-triazolo[1, 5-c]pyrimidine

2-Chloro-4-hydrazino-5-methoxypyrimidine water wet cake (83.2 g of 84.0% chlorohydrazinomethoxy-pyrimidine=69.84 g actual chlorohydrazinomethoxy-pyrimidine, 0.4 mole) was loaded into a 1 L jacketed reactor equipped with a thermocouple temperature probe, overhead stirrer with glass agitator, condenser, addition funnel, and a programmable circulating bath. tert-Butyl alcohol (700 mL) and methanol (100 mL) were added and the mixture was stirred to give a white slurry. A solution of cyanogen bromide (47.19 g, 0.445 mole) in acetonitrile (105 mL) was added dropwise over 20 min. The reaction mixture slurry got thicker and the temperature of the mixture rose from 23° C. to 29° C. The reactor jacket was then heated from 22° C. to 41° C. over 50 min, then held at 41° C. for 6.2 h. During this time the reaction was monitored and the slurry thinned as the reaction proceeded. Once formation of the intermediate triazolo[4,3-c]pyrimidine was complete, the reaction mixture (a light yellow slurry) was transferred using a peristaltic pump via a PTFE dip tube into a 2 L three necked flask containing 30% sodium methoxide in methanol (181.0 g, 1.00 mole). The 2 L flask was cooled in an ice bath. Transfer took place over 52 min, and resulted in the reaction temperature increasing from 21° C. to a maximum of 28° C. The transfer was completed with additional methanol (120 mL) to rinse the transfer tubing into the reactor. The resulting reaction mixture was a dark olive green slurry. After stirring for 1 hour at ambient temperature, the reaction mixture was quenched by dropwise addition of a dilute hydrochloric acid solution (15.1 g of concentrated hydrochloric acid diluted with 300 mL of water). The pH of the resulting slurry was adjusted to 8.50 using 6 N hydrochloric acid (6.3 g). A distillation head was attached, and the volatiles were distilled out of the reaction mixture under reduced pressure (110 mmHg). As distillate was removed, additional water was added to effect a solvent exchange from alcohol to water. A total of 1029 g of distillate was removed, and an additional 500 mL of water was added during the course of the distillation. The mixture was allowed to cool slowly with stirring overnight. The solids were recovered by filtration through Whatman #52 paper using a Buchner funnel and aspirator vacuum. The solids were washed with water (211 g), then dried overnight in vacuo at 83° C. to give the product as a medium brown powdery solid (66.3 g of 95.7% pure 2-amino-5,8-dimethoxy[1,2,4]triazolo[1,5-c] pyrimidine, 82.4% yield).

What is claimed is:

1. A process for the preparation of a compound of the formula

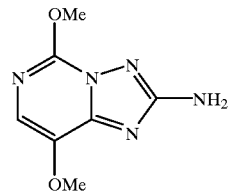

which comprises contacting a 3-amino-8-methoxy-[1,2,4] triazolo[4,3-c]pyrimidine of the formula

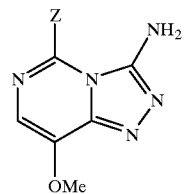

wherein Z represents Cl or $OCH_3$ with sodium or potassium methoxide in an alcohol solvent.

2. The process of claim 1 in which the alcohol solvent is methanol used either alone or in admixture with a tertiary-alcohol.

3. The process of claim 1 in which the 3-amino-8-methoxy[1,2,4]triazolo[4,3-c]pyrimidine of the formula

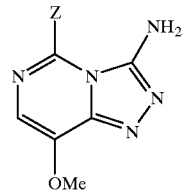

wherein Z represents Cl or $OCH_3$ is prepared by:

a) contacting a 5-methoxy-4-chloropyrimidine of the formula

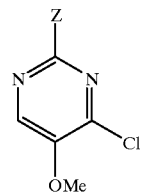

wherein Z is as previously defined with hydrazine and an auxiliary base to prepare a 5-methoxy-4-hydrazinopyrimidine of the formula

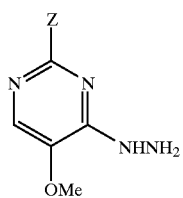

wherein Z is as previously defined; and b) contacting the 5-methoxy-4-hydrazinopyrimidine with cyanogen chloride or cyanogen bromide.

4. The process of claim 3 in which the 3-amino-8-methoxy[1,2,4]triazolo[4,3-c]pyrimidine prepared by contacting the 5-methoxy-4-hydrazino-pyrimidine with cyanogen chloride or cyanogen bromide is treated directly with sodium or potassium methoxide in an alcohol solvent without isolation to prepare the compound of formula

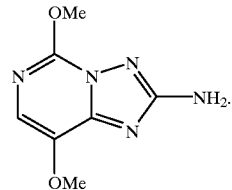

* * * * *